(12) United States Patent
Chiu et al.

(10) Patent No.: US 9,642,546 B2
(45) Date of Patent: May 9, 2017

(54) RELAXATION STATE EVALUATION SYSTEM AND METHOD AND COMPUTER PROGRAM PRODUCT THEREOF

(71) Applicant: National Tsing Hua University, Hsinchu (TW)

(72) Inventors: Hung-Chih Chiu, Hsinchu (TW); Yi-Lwun Ho, Hsinchu (TW); Yen-Hung Lin, Hsinchu (TW); Hsi-Pin Ma, Hsinchu (TW); Tzung-Dau Wang, Hsinchu (TW); Chun-Chieh Chan, Hsinchu (TW); Hung-Chun Lu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 306 days.

(21) Appl. No.: 14/645,141

(22) Filed: Mar. 11, 2015

(65) Prior Publication Data
US 2016/0113538 A1    Apr. 28, 2016

(30) Foreign Application Priority Data
Oct. 24, 2014   (TW) .............................. 103136832 A

(51) Int. Cl.
| A61B 5/04 | (2006.01) |
| A61B 5/0456 | (2006.01) |
| A61B 5/0452 | (2006.01) |
| A61B 5/16 | (2006.01) |
| A61B 5/00 | (2006.01) |
| A61B 5/024 | (2006.01) |

(52) U.S. Cl.
CPC ........ *A61B 5/04012* (2013.01); *A61B 5/0452* (2013.01); *A61B 5/165* (2013.01); *A61B 5/4848* (2013.01); *A61B 5/02405* (2013.01)

(58) Field of Classification Search
CPC ...................................................... A61B 5/04
USPC ......................................................... 600/521
See application file for complete search history.

(56) References Cited

U.S. PATENT DOCUMENTS

2016/0113538 A1* 4/2016 Chiu .................. A61B 5/04012
600/521

* cited by examiner

*Primary Examiner* — Carl H Layno
*Assistant Examiner* — Jon Eric C Morales
(74) *Attorney, Agent, or Firm* — Muncy, Geissler, Olds & Lowe, P.C.

(57) ABSTRACT

The present invention proposes a relaxation state evaluation system and method and a computer program product thereof. The method comprises steps: measuring ECG data of a user; analyzing the ECG data to generate a first, second, third and fourth parameters, wherein the first parameter is the short-scale entropy slope of the user before cardiovascular disease treatment (CVDT); the second parameter is the difference of the post-CVDT and pre-CVDT mean RR intervals; the third parameter is the logarithm of the variance of the pre-CVDT high frequency NN intervals; the fourth parameter is the logarithm of the ratio of the variances of the pre-CVDT low frequency and high frequency NN intervals; working out an evaluation index, which is a function of the abovementioned parameters; and evaluating the relaxation state of the user, wherein the user is determined to be in a relaxation state if the evaluation index is over a threshold.

36 Claims, 2 Drawing Sheets

RELAXATION STATE EVALUATION SYSTEM AND METHOD AND COMPUTER PROGRAM PRODUCT THEREOF

BACKGROUND OF THE INVENTION

1. Field of the Invention

The present invention relates to a relaxation state evaluation system and method and a computer program product thereof, particularly to an ECG-based relaxation state evaluation system and method and a computer program product thereof.

2. Description of the Prior Art

Psychiatric stress has been one of the disease-inducing factors of modern people. If a person is not relaxed appropriately, accumulated stress or fatigue may affect performance of his body and impair functions of organs. Traditionally, the relaxation state of a testee is evaluated with brainwave-based indexes. However, brainwave signals are hard to detect and likely to be interfered with. Therefore, brainwave measurement needs precision devices and a special environment. Thus, a user is inconvenient or even impossible to anytime learn his relaxation state with the brainwave-based technology.

Accordingly, the present invention proposes a non-brainwave-based technology to evaluate the relaxation state.

SUMMARY OF THE INVENTION

The present invention provides a relaxation state evaluation system and method and a computer program product thereof, wherein the electrocardiograph (ECG) data is processed statistically to establish an ECG-based index for evaluating the relaxation state of a user. The evaluation index of the present invention is easy to measure, less likely to be interfered with, and favorable for evaluation by users themselves.

One embodiment of the present invention proposes a relaxation state evaluation system comprising a sensor module and an evaluation module. The sensor module measures ECG data of a user. The evaluation module is electrically connected with the sensor module. The evaluation module analyzes the ECG data measured by the sensor module to generate a first parameter, a second parameter, a third parameter and a fourth parameter, and works out an evaluation index. The first parameter is the short-scale entropy slope before cardiovascular disease treatment (CVDT). The second parameter is the difference of the post-CVDT mean RR interval and the pre-CVDT mean RR interval. The third parameter is the logarithm of the variance of the pre-CVDT high frequency normal to normal (NN) intervals. The fourth parameter is the logarithm of the ratio of the variance of the pre-CVDT low frequency NN intervals to the variance of the pre-CVDT high frequency NN intervals. The evaluation index is a function of the first, second, third and fourth parameters. While the evaluation index is over a threshold, the user is determined to be in a relaxation state.

Another embodiment of the present invention proposes a relaxation state evaluation method comprising steps: measuring ECG data of a user; analyzing the ECG data to generate a first parameter, a second parameter, a third parameter and a fourth parameter, wherein the first parameter is the short-scale entropy slope of a user before cardiovascular disease treatment (CVDT); the second parameter is the difference of the post-CVDT mean RR interval and the pre-CVDT mean RR interval; the third parameter is the logarithm of the variance of the pre-CVDT high frequency NN intervals; the fourth parameter is the logarithm of the ratio of the variance of the pre-CVDT low frequency NN intervals to the variance of the pre-CVDT high frequency NN intervals; working out an evaluation index, wherein the evaluation index is a function of the first, second, third and fourth parameters; and evaluating the relaxation state of the user, wherein the user is determined to be in a relaxation state if the evaluation index is over a threshold.

A further embodiment of the present invention proposes a computer program product recorded in a non-volatile computer-readable medium and loaded into a computation device to execute a relaxation state evaluation method, wherein the relaxation state evaluation method comprises steps: measuring ECG data of a user; analyzing the ECG data to generate a first parameter, a second parameter, a third parameter and a fourth parameter, wherein the first parameter is the short-scale entropy slope of a user before cardiovascular disease treatment (CVDT); the second parameter is the difference of the post-CVDT mean RR interval and the pre-CVDT mean RR interval; the third parameter is the logarithm of the variance of the pre-CVDT high frequency normal to normal (NN) intervals; the fourth parameter is the logarithm of the ratio of the variance of the pre-CVDT low frequency NN intervals to the variance of the pre-CVDT high frequency NN intervals; working out an evaluation index, wherein the evaluation index is a function of the first, second, third and fourth parameters; and evaluating the relaxation state of the user, wherein the user is determined to be in a relaxation state if the evaluation index is over a threshold.

DESCRIPTION OF THE PREFERRED EMBODIMENT

The evaluation index used by the present invention is based on ECG data. A non-linear numerical analysis method is used to find out the non-linear characteristics of the ECG data. The non-linear numerical analysis method used by the present invention includes a multi-scale entropy analysis (MSE analysis) method and a heart rate variability (HRV) de-trended fluctuation analysis method. The MSE analysis method calculates the area-related parameter and the slope-related parameter of the signals to present the short-term complexity and long-term complexity of the signals. The HRV de-trended fluctuation analysis method is used to quantify the correlation of the long-term RR intervals and the short-term RR intervals. The present invention adopts a characteristic normalization method to overcome the limit of the conventional normalization method. The characteristic normalization method undertakes normalization according to the symmetry of signal probability distribution and is able to effectively reduce the distortion occurring in the normalization of the original signals.

The linear regression analysis of the statistics can be used to establish an equation to prove the high correlation between electrocardiograph (ECG) and electroencephalogram (EEG). Firstly, a linear method and a non-linear method are used to respectively quantify ECG and EEG.

Next, some parameters, such as the age, medicine treatment, and surgical history of the testee, are introduced into the equations; a Spearman correlation method is used to eliminate high-correlation variables. Next, a stepwise variable selection method is used to find out the most suitable variables. Then, a linear regression method is used to establish a desired equation. Finally, a multiple R method is used to prove the reliability of the intercourse between EEG and ECG.

Figure 1:
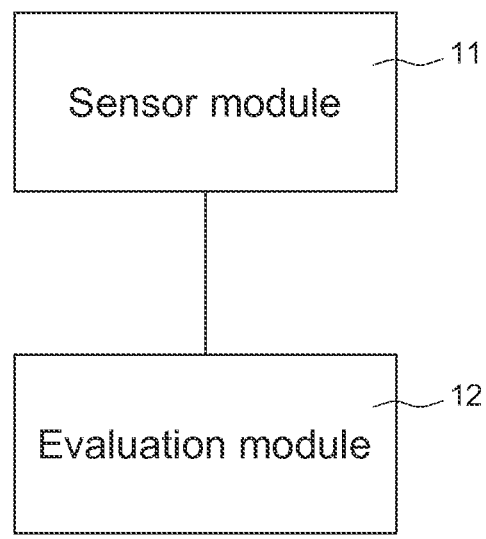
FIG. 1 is a block diagram schematically showing a relaxation state evaluation system according to one embodiment of the present invention.

Refer to FIG. 1 schematically showing a relaxation state evaluation system according to one embodiment of the present invention. The relaxation state evaluation system of the present invention comprises a sensor module 11 and an evaluation module 12. The sensor module 11 measures ECG data of a user. For example, the sensor module 12 measures heartbeat signals, pulse rate and blood oxygen concentration and acquires corresponding ECG data. The measurement duration ranges from 5 minutes to 24 hours. The evaluation module 12 is electrically connected with the sensor module 11. The evaluation module 12 analyzes the ECG data measured by the sensor module 11 and processes the ECG data statistically to generate a first parameter, a second parameter, a third parameter and a fourth parameter. The first parameter is the short-scale entropy slope, wherein the multi-scale entropy analysis method processes the ECG data obtained before the cardiovascular disease treatment (CVDT) of the user to output the short-scale entropy slope. The second parameter is the difference of the post-CVDT mean RR interval and the pre-CVDT mean RR interval. The third parameter is the logarithm of the variance of the pre-CVDT high frequency normal to normal (NN) intervals. The high frequency is referred to that the signals are captured at a frequency of 0.15-0.4 Hz. The third parameter is an index of the activity of the parasympathetic nerve. The fourth parameter is the logarithm of the ratio of the variance of the pre-CVDT low frequency NN intervals to the variance of the pre-CVDT high frequency NN intervals. The low frequency is referred to that the signals are captured at a frequency of 0.04-0.15 Hz. The fourth parameter is an index of the simultaneous regulation of the sympathetic nerve and the parasympathetic nerve.

Next, the evaluation module 12 works out an evaluation index according to the first, second, third and fourth parameters. For example, the evaluation index is a function of the first, second, third and fourth parameters. The evaluation module 12 determines that the user is in a relaxation state if the evaluation index is over a threshold.

In a first embodiment, the evaluation index is calculated according to Equation (1):

$$A0+A1\times PA1+A2\times PA2+A3\times PA3+A4\times PA4 \qquad (1)$$

wherein PA1-PA4 are respectively the first, second, third and fourth parameters; A0-A4 are coefficients. The coefficients A0-A4 vary with different samples in database. For example, the ethnic group, age, sex, cardiovascular disease medicine treatment, cardiovascular surgery of a sample may vary the coefficients A0-A4. However, the coefficients A0-A4 may be constant values if the quantity of samples is large enough. The same characteristic will also appear in other embodiments and will not repeat thereinafter.

In the first embodiment, the evaluation index varies within the range of −7.2465 to 8.4435. If the evaluation index is over 0.5985, the user is determined to be in a relaxation state. Table. 1 shows the statistical significance analysis (i.e. the P values) of the first, second, third and fourth parameters to the evaluation index. The comparison and analysis of ECG signals and EEG signals shows that the multiple R value is 0.53, which indicates that synchronicity correlation exists in ECG signals and EEG signals.

TABLE 1

| Parameter | P value |
| --- | --- |
| First Parameter | $3.88 \times 10^{-5}$ *** |
| Second Parameter | 0.02452 * |
| Third Parameter | 0.02040 * |
| Fourth Parameter | 0.00243 ** |

*** $p < 0.001$
** $p < 0.01$
* $p < 0.05$

In a second embodiment, the evaluation index is calculated according to Equation (2):

$$A0+A1\times PA1+A2\times PA2+A3\times PA3+A4\times PA4+A5\times PA5 \qquad (2)$$

wherein A5 is a coefficient and PA5 is a fifth parameter. The other symbols in Equation (2) have the same meanings as those in Equation (1) and will not repeat herein. The fifth parameter is the long-scale entropy slope, wherein the multi-scale entropy analysis method processes the ECG data obtained before the cardiovascular disease treatment (CVDT) of the user to output the long-scale entropy slope.

In the second embodiment, the evaluation index varies within the range of −11.0056 to 11.0665. If the evaluation index is over 0.0305, the user is determined to be in a relaxation state. Table. 2 shows the statistical significance analysis (i.e. the P values) of the first, second, third, fourth and fifth parameters to the evaluation index. The comparison and analysis of ECG signals and EEG signals shows that the multiple R value is 0.554, which indicates that synchronicity correlation exists in ECG signals and EEG signals.

TABLE 2

| Parameter | P value |
| --- | --- |
| First Parameter | $1.5 \times 10^{-5}$ *** |
| Second Parameter | 0.01178 * |
| Third Parameter | 0.00989 ** |
| Fourth Parameter | 0.07386 |
| Fifth Parameter | 0.00162 ** |

*** $p < 0.001$
** $p < 0.01$
* $p < 0.05$

In a third embodiment, the evaluation index is calculated according to Equation (3):

$$A0+A1\times PA1+A2\times PA2+A3\times PA3+A4\times PA4+A5\times PA5+ \\ A6\times PA6 \qquad (3)$$

wherein A6 is a coefficient and PA6 is a sixth parameter. The other symbols in Equation (3) have the same meanings as those in Equation (2) and will not repeat herein. The sixth parameter is the logarithm of the difference of the post-CVDT NN interval over 20 ms and the pre-CVDT NN interval over 20 ms.

In the third embodiment, the evaluation index varies within the range of −10.2559 to 9.5578. If the evaluation index is over −0.3491, the user is determined to be in a relaxation state. Table. 3 shows the statistical significance analysis (i.e. the P values) of from the first parameter to the sixth parameter to the evaluation index. The comparison and analysis of ECG signals and EEG signals shows that the multiple R value is 0.5637, which indicates that synchronicity correlation exists in ECG signals and EEG signals.

TABLE 3

| Parameter | P value |
|---|---|
| First Parameter | $3.86 \times 10^{-5}$ *** |
| Second Parameter | 0.00624 ** |
| Third Parameter | 0.01276 * |
| Fourth Parameter | 0.06292 |
| Fifth Parameter | 0.00201 ** |
| Sixth Parameter | 0.26881 |

*** $p < 0.001$
** $p < 0.01$
* $p < 0.05$

In a fourth embodiment, the evaluation index is calculated according to Equation (4):

$$A0+A1 \times PA1+A2 \times PA2+A3 \times PA3+A4 \times PA4+A5 \times PA5+A6 \times PA6+A7 \times PA7 \quad (4)$$

wherein A7 is a coefficient and PA7 is a seventh parameter. The other symbols in Equation (4) have the same meanings as those in Equation (3) and will not repeat herein. The seventh parameter is the logarithm of the difference of the standard deviation of the post-CVDT normal sinus rhythm (NSR) interval and the standard deviation of the pre-CVDT NSR interval.

In the fourth embodiment, the evaluation index varies within the range of −12.6167 to 11.5619. If the evaluation index is over −0.5274, the user is determined to be in a relaxation state. Table. 4 shows the statistical significance analysis (i.e. the P values) of from the first parameter to the seventh parameter to the evaluation index. The comparison and analysis of ECG signals and EEG signals shows that the multiple R value is 0.585, which indicates that synchronicity correlation exists in ECG signals and EEG signals.

TABLE 4

| Parameter | P value |
|---|---|
| First Parameter | 0.000112 *** |
| Second Parameter | 0.005271 ** |
| Third Parameter | 0.004063 ** |
| Fourth Parameter | 0.055178 |
| Fifth Parameter | 0.001239 ** |
| Sixth Parameter | 0.078980 |
| Seventh Parameter | 0.092762 |

*** $p < 0.001$
** $p < 0.01$
* $p < 0.05$

In a fifth embodiment, the evaluation index is calculated according to Equation (5):

$$A0+A1 \times PA1+A2 \times PA2+A3 \times PA3+A4 \times PA4+A5 \times PA5+A6 \times PA6+A7 \times PA7+A8 \times PA8 \quad (5)$$

wherein A8 is a coefficient and PA8 is an eighth parameter. The other symbols in Equation (5) have the same meanings as those in Equation (4) and will not repeat herein. The eighth parameter is the difference of the post-CVDT short-scale entropy slope and the pre-CVDT short-scale entropy slope.

In the fifth embodiment, the evaluation index varies within the range of −9.6939 to 7.0790. If the evaluation index is over −1.3075, the user is determined to be in a relaxation state. Table. 5 shows the statistical significance analysis (i.e. the P values) of from the first parameter to the eighth parameter to the evaluation index. The comparison and analysis of ECG signals and EEG signals shows that the multiple R value is 0.603, which indicates that synchronicity correlation exists in ECG signals and EEG signals.

TABLE 5

| Parameter | P value |
|---|---|
| First Parameter | $3.29 \times 10^{-5}$ *** |
| Second Parameter | 0.002694 ** |
| Third Parameter | 0.004240 ** |
| Fourth Parameter | 0.044295 * |
| Fifth Parameter | 0.000551 *** |
| Sixth Parameter | 0.112643 |
| Seventh Parameter | 0.027292 * |
| Eighth Parameter | 0.038786 * |

*** $p < 0.001$
** $p < 0.01$
* $p < 0.05$

It should be easily understood: the physiological status of the user may influence the measured ECG data. Therefore, in one embodiment, the user himself can autonomously input user parameters, which represent the physiological information of the user, including age, whether the user takes cardiovascular disease medicine, and whether the user experienced cardiovascular surgery. Then, the user parameters are taken into consideration in calculating the evaluation index.

In a sixth embodiment, the evaluation index is calculated according to Equation (6):

$$A0+A1 \times PA1+A2 \times PA2+A3 \times PA3+A4 \times PA4+A5 \times PA5+A6 \times PA6+A7 \times PA7+A8 \times PA8+Au1 \times IP1+Au2 \times IP2+Au3 \times IP3+Au4 \times IP4 \quad (6)$$

wherein Au1-Au4 are coefficients; IP1-IP4 are respectively a first input parameter, a second input parameter, a third input parameter and a fourth input parameter. The other symbols in Equation (6) have the same meanings as those in Equation (5) and will not repeat herein. The first input parameter is the glomerular filtration rate used to evaluate the performance of the kidneys of the user and ranging from 60 ml/min/1.73 m² to 90 ml/min/1.73 m². The second input parameter represents that the user takes a vein dilator, such as Isosorbide Dinitrate, Ismo-20, Nithroderm TTS, Sigmant, or Nitroglycerin Nitrostat Sublingual Tablets. The third input parameter represents that the user does not take anticoagulation medicine. The fourth input parameter represents that the user has hypertension.

In the sixth embodiment, the evaluation index varies within the range of −7.7442 to 15.3658. If the evaluation index is over 8.4328, the user is determined to be in a relaxation state. Table. 6 shows the statistical significance analysis (i.e. the P values) of from the first parameter to the eighth parameter and from the first input parameter to the fourth input parameter to the evaluation index. The comparison and analysis of ECG signals and EEG signals shows that the multiple R value is 0.7, which indicates that synchronicity correlation exists in ECG signals and EEG signals.

TABLE 6

| Parameter | P value | Parameter | P value |
|---|---|---|---|
| First Parameter | $1.94 \times 10^{-6}$ *** | First Input Parameter | 0.005196 ** |
| Second Parameter | 0.000746 *** | Second Input Parameter | 0.089860 |
| Third Parameter | 0.004203 ** | Third Input Parameter | 0.086859 |
| Fourth Parameter | 0.008935 ** | Fourth Input Parameter | 0.016642 * |
| Fifth Parameter | 0.000435 *** | | |
| Sixth Parameter | 0.132636 | | |

TABLE 6-continued

| Parameter | P value | Parameter | P value |
|---|---|---|---|
| Seventh Parameter | 0.007233 ** | | |
| Eighth Parameter | 0.059433 | | |

*** $p < 0.001$
** $p < 0.01$
* $p < 0.05$

In a seventh embodiment, the evaluation index is calculated according to Equation (7):

$$A0+A1 \times PA1+A2 \times PA2+A3 \times PA3+A4 \times PA4+A5 \times PA5+ \\ A6 \times PA6+A7 \times PA7+A8 \times PA8+A9 \times PA9 \quad (7)$$

wherein A9 is a coefficient and PA9 is a ninth parameter. The other symbols in Equation (7) have the same meanings as those in Equation (6) and will not repeat herein. The ninth parameter is the difference of the post-CVDT long-scale entropy area and the pre-CVDT long-scale entropy area.

In the seventh embodiment, the evaluation index varies within the range of −10.6144 to 7.4267. If the evaluation index is over −1.5939, the user is determined to be in a relaxation state. Table. 7 shows the statistical significance analysis (i.e. the P values) of from the first parameter to the ninth parameter to the evaluation index. The comparison and analysis of ECG signals and EEG signals shows that the multiple R value is 0.606, which indicates that synchronicity correlation exists in ECG signals and EEG signals.

TABLE 7

| Parameter | P value |
|---|---|
| First Parameter | $6.24 \times 10^{-5}$ *** |
| Second Parameter | 0.003436 *** |
| Third Parameter | 0.004539 *** |
| Fourth Parameter | 0.042849 *** |
| Fifth Parameter | 0.000673 *** |
| Sixth Parameter | 0.091711 *** |
| Seventh Parameter | 0.025573 ** |
| Eighth Parameter | 0.538770 * |
| Ninth Parameter | 0.046492 ** |

*** $p < 0.001$
** $p < 0.01$
* $p < 0.05$

In an eighth embodiment, the evaluation index is calculated according to Equation (8):

$$A0+A1 \times PA1+A2 \times PA2+A3 \times PA3+A4 \times PA4+A5 \times PA5+ \\ A6 \times PA6+A7 \times PA7+A8 \times PA8+A9 \times PA9+Au1 \times \\ IP1+Au2 \times IP2+Au3 \times IP3+Au4 \times IP4 \quad (8)$$

wherein the symbols in Equation (8) have the same meanings as those in Equations (6) and (7) and will not repeat herein.

In the eighth embodiment, the evaluation index varies within the range of −9.2634 to 16.7214. If the evaluation index is over 8.9256, the user is determined to be in a relaxation state. Table. 8 shows the statistical significance analysis (i.e. the P values) of from the first parameter to the ninth parameter and from the first input parameter to the fourth input parameter to the evaluation index. The comparison and analysis of ECG signals and EEG signals shows that the multiple R value is 0.71, which indicates that synchronicity correlation exists in ECG signals and EEG signals.

TABLE 8

| Parameter | P value | Parameter | P value |
|---|---|---|---|
| First Parameter | $6.2 \times 10^{-6}$ *** | First Input Parameter | 0.006020 ** |
| Second Parameter | 0.000911 *** | Second Input Parameter | 0.064310 |
| Third Parameter | 0.005045 ** | Third Input Parameter | 0.052859 |
| Fourth Parameter | 0.007338 ** | Fourth Input Parameter | 0.009471 ** |
| Fifth Parameter | 0.000683 *** | | |
| Sixth Parameter | 0.048188 * | | |
| Seventh Parameter | 0.002599 ** | | |
| Eighth Parameter | 0.160631 | | |
| Ninth Parameter | 0.019518 * | | |

*** $p < 0.001$
** $p < 0.01$
* $p < 0.05$

In a ninth embodiment, the evaluation index is calculated according to Equation (9):

$$A0+A1 \times PA1+A2 \times PA2+A3 \times PA3+A4 \times PA4+A5 \times PA5+ \\ A6 \times PA6+A7 \times PA7+A8 \times PA8+A9 \times PA9+Au1 \times \\ IP1+Au2 \times IP2+Au3 \times IP3+Au4 \times IP4+Au5 \times IP5+ \\ Au6 \times IP6+Au7 \times IP7+Au8 \times IP8+Au9 \times IP9+Au10 \times \\ IP10+Au11 \times IP11+Au12 \times IP12+Au13 \times IP13+ \\ Au14 \times IP14 \quad (9)$$

wherein Au5-Au14 are coefficients; IP5-IP14 are respectively a fifth input parameter, a sixth input parameter, a seventh input parameter, an eighth input parameter, a ninth input parameter, a tenth input parameter, a eleventh input parameter, a twelfth input parameter, a thirteenth input parameter and a fourteenth input parameter. The other symbols in Equation (9) have the same meanings as those in Equation (8) and will not repeat herein. The fifth input parameter represents that the user does not take Digitalis Glycoside (such as Digoxin), which is suitable for heart failure, atrial flutter, atrial fibrillation, and paroxysmal supraventricular tachycardia. The sixth input parameter is the age of the user. The seventh input parameter is the pre-CVDT blood pressure. The eighth input parameter represents that the user suffers hyperlipidemia. The ninth input parameter represents that the user does not take a vein dilator. The tenth input parameter represents that the user takes an anticoagulation medicine (such as Bokey, Plavix, or Tapal). The eleventh input parameter represents that the user suffers a peripheral arterial occlusion disease and has accepted balloon dilation. The twelfth input parameter represents that the user suffers a coronary artery disease but has not accepted cardiac catheterization yet. The thirteenth input parameter represents that the user takes an anti-hyperlipidemia medicine, such as Zocor, Lipitor, Crestor, Mevalotin, or Lescol. The fourteenth input parameter represents that the user suffers vessel occlusion but has not accepted cardiac catheterization and balloon dilation yet.

In the ninth embodiment, the evaluation index varies within the range of −5.4138 to 8.6076. If the evaluation index is over 4.4012, the user is determined to be in a relaxation state. Table. 9 shows the statistical significance analysis (i.e. the P values) of from the first parameter to the ninth parameter and from the first input parameter to the fourteenth input parameter to the evaluation index. The comparison and analysis of ECG signals and EEG signals shows that the multiple R value is 0.88, which indicates that synchronicity correlation exists in ECG signals and EEG signals.

TABLE 9

| Parameter | P value | Parameter | P value |
|---|---|---|---|
| First Parameter | $7.35 \times 10^{-10}$ *** | First Input Parameter | $2.59 \times 10^{-7}$ *** |
| Second Parameter | 4.45e−08 *** | Second Input Parameter | 0.003830 ** |
| Third Parameter | 0.000730 *** | Third Input Parameter | 8.97e−06 *** |
| Fourth Parameter | 0.000253 *** | Fourth Input Parameter | 3.29e−06 *** |
| Fifth Parameter | 1.91e−06 *** | Fifth Input Parameter | 0.000343 *** |
| Sixth Parameter | 7.96e−05 *** | Sixth Input Parameter | 0.000420 *** |
| Seventh Parameter | 0.002486 ** | Seventh Input Parameter | 0.002746 ** |
| Eighth Parameter | 0.028980 * | Eighth Input Parameter | 0.013978 * |
| Ninth Parameter | 0.002884 ** | Ninth Input Parameter | 0.000289 *** |
|  |  | Tenth Input Parameter | 0.007853 ** |
|  |  | Eleventh Input Parameter | 0.001109 ** |
|  |  | Twelfth Input Parameter | 0.001689 ** |
|  |  | Thirteenth Input Parameter | 0.011285 * |
|  |  | Fourteenth Input Parameter | 0.049927 * |

*** $p < 0.001$
** $p < 0.01$
* $p < 0.05$

In the abovementioned embodiments, the evaluation indexes respectively vary in different ranges and respectively have different threshold values. It should be easily understood that normalizing the evaluation indexes will converges the threshold values. For example, after normalizing the evaluation indexes, the threshold values of the first embodiment to the fifth embodiment and the seventh embodiment are set to be 0.5; the threshold values of the sixth, eighth and ninth embodiments are also set to be 0.5.

In present invention, the evaluation module 12 communicates with the sensor module 11 in a wired or wireless way. In one embodiment, the sensor module 11 has a Bluetooth module or a WLAN module and transmits the measured ECG data to the evaluation module 12 wirelessly. In the present invention, the evaluation module 12 is a single device or a combination of several devices. For example, the evaluation module 12 is a computer, a portable device or a mobile Internet access device (such as a mobile phone or a tablet computer). Alternatively, the evaluation module 12 is a combination of a cloud server and a computer or a mobile Internet access device. Thereby, the computer or mobile Internet access device can collect ECG data measured by the sensor module 11 or the parameters input by the user and transmit the data to the cloud server. After completing analysis and evaluation, the cloud server transmits the results to the computer or mobile Internet access device. Then, the computer or mobile Internet access device presents the results to the user.

Figure 2:
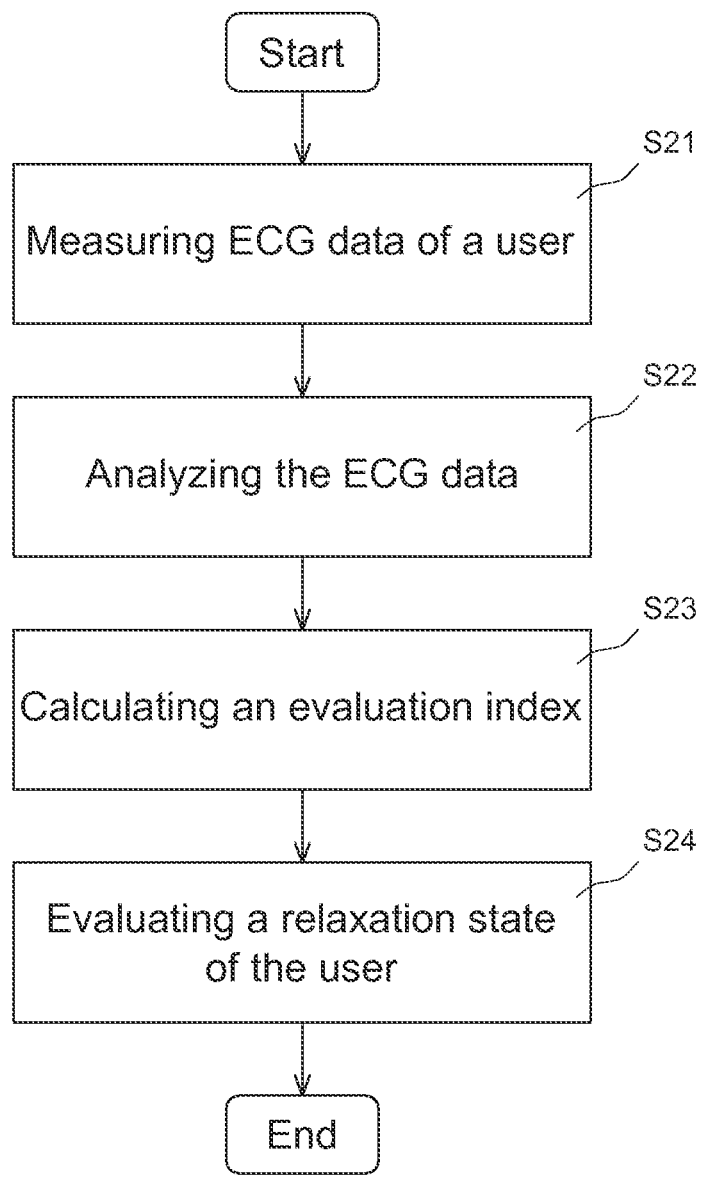
FIG. 2 is a flowchart schematically showing a relaxation state evaluation method according to one embodiment of the present invention.

Refer to FIG. 2 showing a flowchart of a relaxation state evaluation method according to one embodiment of the present invention. In Step S21, measure ECG data of a user. Next, in Step S22, analyze the ECG data to generate required parameters, such as the first parameter to the fourth parameter mentioned in the first embodiment. Next, in Step S23, calculate an evaluation index, which is a function of the parameters generated in Step S22. Then, in Step S24, evaluate the relaxation state of the user; for example, the user is determined to be in a relaxation state if the evaluation index is over a threshold. The details have been described above and will not repeat herein.

In one embodiment, the program of the evaluation method of the present invention is recorded in a non-volatile computer-readable medium to form a computer program product, which can be loaded into a computation device. Thus, the computation device can execute the relaxation state evaluation method shown in FIG. 2. The details of the relaxation state evaluation method of the present invention have been described above and will not repeat herein.

In conclusion, the evaluation index used by the relaxation state evaluation system and method and the computer program product thereof is obtained via processing ECG data statistically. Therefore, the present invention can evaluate the relaxation state of a user merely using the ECG data of the user. In comparison with the measurement of EEG, the measurement of ECG is easy and less likely to be affected. Therefore, the present invention can be operated by users themselves and favors the popularization of personal relaxation state evaluation systems.

What is claimed is:

1. A relaxation state evaluation system comprising
a sensor module measuring electrocardiograph (ECG) data of a user; and
an evaluation module electrically connected with the sensor module, analyzing the ECG data to generate a first parameter, a second parameter, a third parameter and a fourth parameter, and working out an evaluation index,
wherein the first parameter is a short-scale entropy slope before a cardiovascular disease treatment (CVDT) of the user; the second parameter is a difference of a post-CVDT mean RR interval and a pre-CVDT mean RR interval; the third parameter is a logarithm of a variance of a pre-CVDT high frequency normal to normal (NN) intervals; the fourth parameter is a logarithm of a ratio of a variance of a pre-CVDT low frequency NN intervals to the variance of the pre-CVDT high frequency NN intervals; the evaluation index is a function of the first parameter, the second parameter, the third parameter and the fourth parameter; the user is determined to in a relaxation state if the evaluation index is over a threshold.

2. The relaxation state evaluation system according to claim 1, wherein the evaluation index is calculated according to Equation (1):

$$A0 + A1 \times PA1 + A2 \times PA2 + A3 \times PA3 + A4 \times PA4 \quad (1)$$

wherein A0-A4 are coefficients; PA1-PA4 are respectively the first parameter, the second parameter, the third parameter and the fourth parameter.

3. The relaxation state evaluation system according to claim 2, wherein the function for calculating the evaluation index further includes a fifth parameter, which is a pre-CVDT long-scale entropy slope; the evaluation index is calculated according to Equation (2):

$$A0 + A1 \times PA1 + A2 \times PA2 + A3 \times PA3 + A4 \times PA4 + A5 \times PA5 \quad (2)$$

wherein A5 is a coefficient and PA5 is the fifth parameter.

4. The relaxation state evaluation system according to claim 3, wherein the function for calculating the evaluation index further includes a sixth parameter, which is a logarithm of a difference of a post-CVDT NN interval over 20 ms and a pre-CVDT NN interval over 20 ms; the evaluation index is calculated according to Equation (3):

$$A0+A1\times PA1+A2\times PA2+A3\times PA3+A4\times PA4+A5\times PA5+A6\times PA \quad (3)$$

wherein A6 is a coefficient and PA6 is the sixth parameter.

5. The relaxation state evaluation system according to claim 4, wherein the function for calculating the evaluation index further includes a seventh parameter, which is a logarithm of a difference of a standard deviation of a post-CVDT normal sinus rhythm (NSR) interval and a standard deviation of a pre-CVDT NSR interval; the evaluation index is calculated according to Equation (4):

$$A0+A1\times PA1+A2\times PA2+A3\times PA3+A4\times PA4+A5\times PA5+A6\times PA6+A7\times PA7 \quad (4)$$

wherein A7 is a coefficient and PA7 is the seventh parameter.

6. The relaxation state evaluation system according to claim 5, wherein the function for calculating the evaluation index further includes an eighth parameter, which is a difference of a post-CVDT short-scale entropy slope and a pre-CVDT short-scale entropy slop; the evaluation index is calculated according to Equation (5):

$$A0+A1\times PA1+A2\times PA2+A3\times PA3+A4\times PA4+A5\times PA5+A6\times PA6+A7\times PA7+A8\times PA8 \quad (5)$$

wherein A8 is a coefficient and PA8 is the eighth parameter.

7. The relaxation state evaluation system according to claim 6, wherein the evaluation index is also dependent on user parameters, which represent physiological data of the user.

8. The relaxation state evaluation system according to claim 7, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (6):

$$A0+A1\times PA1+A2\times PA2+A3\times PA3+A4\times PA4+A5\times PA5+A6\times PA6+A7\times PA7+A8\times PA8+Au1\times IP1+Au2\times IP2+Au3\times IP3+Au4\times IP4 \quad (6)$$

wherein Au1-Au4 are coefficients; IP1-IP4 are respectively the first input parameter, the second input parameter, the third input parameter and the fourth input parameter.

9. The relaxation state evaluation system according to claim 6, wherein the function for calculating the evaluation index further includes a ninth parameter, which is a difference of a post-CVDT long-scale entropy area and a pre-CVDT long-scale entropy area; the evaluation index is calculated according to Equation (7):

$$A0+A1\times PA1+A2\times PA2+A3\times PA3+A4\times PA4+A5\times PA5+A6\times PA6+A7\times PA7+A8\times PA8+A9\times PA9 \quad (7)$$

wherein A9 is a coefficient and PA9 is the ninth parameter.

10. The relaxation state evaluation system according to claim 9, wherein the evaluation index is also dependent on user parameters, which represent physiological data of the user.

11. The relaxation state evaluation system according to claim 10, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (8):

$$A0+A1\times PA1+A2\times PA2+A3\times PA3+A4\times PA4+A5\times PA5+A6\times PA6+A7\times PA7+A8\times PA8+A9\times PA9+Au1\times IP1+Au2\times IP2+Au3\times IP3+Au4\times IP4 \quad (8)$$

wherein Au1-Au4 are coefficients; IP1-IP4 are respectively the first input parameter, the second input parameter, the third input parameter and the fourth input parameter.

12. The relaxation state evaluation system according to claim 11, wherein the user parameters includes a fifth input parameter, a sixth input parameter, a seventh input parameter, an eighth input parameter, a ninth input parameter, a tenth input parameter, a eleventh input parameter, a twelfth input parameter, a thirteenth input parameter and a fourteenth input parameter; the fifth input parameter represents that the user does not take Digitalis Glycoside; the sixth input parameter is age of the user; the seventh input parameter is a pre-CVDT blood pressure of the user; the eighth input parameter represents that the user suffers hyperlipidemia; the ninth input parameter represents that the user does not take a vein dilator; the tenth input parameter represents that the user takes an anticoagulation medicine; the eleventh input parameter represents that the user suffers a peripheral arterial occlusion disease and has accepted balloon dilation; the twelfth input parameter represents that the user suffers a coronary artery disease but has not accepted cardiac catheterization yet; the thirteenth input parameter represents that the user takes an anti-hyperlipidemia medicine; the fourteenth input parameter represents that the user suffers vessel occlusion but has not accepted cardiac catheterization and balloon dilation yet; the evaluation index is calculated according to Equation (9):

$$A0+A1\times PA1+A2\times PA2+A3\times PA3+A4\times PA4+A5\times PA5+A6\times PA6+A7\times PA7+A8\times PA8+A9\times PA9+Au1\times IP1+Au2\times IP2+Au3\times IP3+Au4\times IP4+Au5\times IP5+Au6\times IP6+Au7\times IP7+Au8\times IP8+Au9\times IP9+Au10\times IP10+Au11\times IP11+Au12\times IP12+Au13\times IP13+Au14\times IP14 \quad (9)$$

wherein Au5-Au14 are coefficients; IP5-IP14 are respectively the fifth input parameter, the sixth input parameter, the seventh input parameter, an eighth input parameter, the ninth input parameter, the tenth input parameter, the eleventh input parameter, the twelfth input parameter, the thirteenth input parameter and the fourteenth input parameter.

13. A relaxation state evaluation method comprising steps:
measuring electrocardiograph (ECG) data of a user;
analyzing the ECG data to generate a first parameter, a second parameter, a third parameter and a fourth parameter, wherein the first parameter is a short-scale entropy slope before a cardiovascular disease treatment (CVDT) of the user; the second parameter is a difference of a post-CVDT mean RR interval and a pre-CVDT mean RR interval; the third parameter is a logarithm of a variance of a pre-CVDT high frequency normal to normal (NN) intervals; the fourth parameter is a logarithm of a ratio of a variance of a pre-CVDT low frequency NN intervals to the variance of the pre-CVDT high frequency NN intervals; the evaluation index is a function of the first parameter, the second parameter, the third parameter and the fourth parameter; the user is determined to in a relaxation state if the evaluation index is over a threshold;

calculating an evaluation index, which is a function of the first parameter, the second parameter, the third parameter and the fourth parameter; and evaluating a relaxation state of the user, wherein the user is determined to be in a relaxation state if the evaluation index is over a threshold.

14. The relaxation state evaluation method according to claim 13, wherein the evaluation index is calculated according to Equation (1):

$$A0+A1\times PA1+A2\times PA2+A3\times PA3+A4\times PA4 \quad (1)$$

wherein A0-A4 are coefficients; PA1-PA4 are respectively the first parameter, the second parameter, the third parameter and the fourth parameter.

15. The relaxation state evaluation method according to claim 14, wherein the function for calculating the evaluation index further includes a fifth parameter, which is a pre-CVDT long-scale entropy slope; the evaluation index is calculated according to Equation (2):

$$A0+A1\times PA1+A2\times PA2+A3\times PA3+A4\times PA4+A5\times PA5 \quad (2)$$

wherein A5 is a coefficient and PA5 is the fifth parameter.

16. The relaxation state evaluation method according to claim 15, wherein the function for calculating the evaluation index further includes a sixth parameter, which is a logarithm of a difference of a post-CVDT NN interval over 20 ms and a pre-CVDT NN interval over 20 ms; the evaluation index is calculated according to Equation (3):

$$A0+A1\times PA1+A2\times PA2+A3\times PA3+A4\times PA4+A5\times PA5+ \\ A6\times PA \quad (3)$$

wherein A6 is a coefficient and PA6 is the sixth parameter.

17. The relaxation state evaluation method according to claim 16, wherein the function for calculating the evaluation index further includes a seventh parameter, which is a logarithm of a difference of a standard deviation of a post-CVDT normal sinus rhythm (NSR) interval and a standard deviation of a pre-CVDT NSR interval; the evaluation index is calculated according to Equation (4):

$$A0+A1\times PA1+A2\times PA2+A3\times PA3+A4\times PA4+A5\times PA5+ \\ A6\times PA6+A7\times PA7 \quad (4)$$

wherein A7 is a coefficient and PA7 is the seventh parameter.

18. The relaxation state evaluation method according to claim 17, wherein the function for calculating the evaluation index further includes an eighth parameter, which is a difference of a post-CVDT short-scale entropy slope and a pre-CVDT short-scale entropy slop; the evaluation index is calculated according to Equation (5):

$$A0+A1\times PA1+A2\times PA2+A3\times PA3+A4\times PA4+A5\times PA5+ \\ A6\times PA6+A7\times PA7+A8\times PA8 \quad (5)$$

wherein A8 is a coefficient and PA8 is the eighth parameter.

19. The relaxation state evaluation method according to claim 18, wherein the evaluation index is also dependent on user parameters, which represent physiological data of the user.

20. The relaxation state evaluation method according to claim 19, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (6):

$$A0+A1\times PA1+A2\times PA2+A3\times PA3+A4\times PA4+A5\times PA5+ \\ A6\times PA6+A7\times PA7+A8\times PA8+Au1\times IP1+Au2\times \\ IP2+Au3\times IP3+Au4\times IP4 \quad (6)$$

wherein Au1-Au4 are coefficients; IP1-IP4 are respectively the first input parameter, the second input parameter, the third input parameter and the fourth input parameter.

21. The relaxation state evaluation method according to claim 18, wherein the function for calculating the evaluation index further includes a ninth parameter, which is a difference of a post-CVDT long-scale entropy area and a pre-CVDT long-scale entropy area; the evaluation index is calculated according to Equation (7):

$$A0+A1\times PA1+A2\times PA2+A3\times PA3+A4\times PA4+A5\times PA5+ \\ A6\times PA6+A7\times PA7+A8\times PA8+A9\times PA9 \quad (7)$$

wherein A9 is a coefficient and PA9 is the ninth parameter.

22. The relaxation state evaluation method according to claim 21, wherein the evaluation index is also dependent on user parameters, which represent physiological data of the user.

23. The relaxation state evaluation method according to claim 22, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (8):

$$A0+A1\times PA1+A2\times PA2+A3\times PA3+A4\times PA4+A5\times PA5+ \\ A6\times PA6+A7\times PA7+A8\times PA8+A9\times PA9+Au1\times \\ IP1+Au2\times IP2+Au3\times IP3+Au4\times IP4 \quad (8)$$

wherein Au1-Au4 are coefficients; IP1-IP4 are respectively the first input parameter, the second input parameter, the third input parameter and the fourth input parameter.

24. The relaxation state evaluation method according to claim 23, wherein the user parameters includes a fifth input parameter, a sixth input parameter, a seventh input parameter, an eighth input parameter, a ninth input parameter, a tenth input parameter, a eleventh input parameter, a twelfth input parameter, a thirteenth input parameter and a fourteenth input parameter; the fifth input parameter represents that the user does not take Digitalis Glycoside; the sixth input parameter is age of the user; the seventh input parameter is a pre-CVDT blood pressure of the user; the eighth input parameter represents that the user suffers hyperlipidemia; the ninth input parameter represents that the user does not take a vein dilator; the tenth input parameter represents that the user takes an anticoagulation medicine; the eleventh input parameter represents that the user suffers a peripheral arterial occlusion disease and has accepted balloon dilation; the twelfth input parameter represents that the user suffers a coronary artery disease but has not accepted cardiac catheterization yet; the thirteenth input parameter represents that the user takes an anti-hyperlipidemia medicine; the fourteenth input parameter represents that the user suffers vessel occlusion but has not accepted cardiac catheterization and balloon dilation yet; the evaluation index is calculated according to Equation (9):

$$A0+A1{\times}PA1+A2{\times}PA2+A3{\times}PA3+A4{\times}PA4+A5{\times}PA5+\\A6{\times}PA6+A7{\times}PA7+A8{\times}PA8+A9{\times}PA9+Au1{\times}\\IP1+Au2{\times}IP2+Au3{\times}IP3+Au4{\times}IP4+Au5{\times}IP5+\\Au6{\times}IP6+Au7{\times}IP7+Au8{\times}IP8+Au9{\times}IP9+Au10{\times}\\IP10+Au11{\times}IP11+Au12{\times}IP12+Au13{\times}IP13+\\Au14{\times}IP14 \quad (9)$$

wherein Au5-Au14 are coefficients; IP5-IP14 are respectively the fifth input parameter, the sixth input parameter, the seventh input parameter, an eighth input parameter, the ninth input parameter, the tenth input parameter, the eleventh input parameter, the twelfth input parameter, the thirteenth input parameter and the fourteenth input parameter.

25. A computer program product, which is recorded in a non-volatile computer-readable medium and loaded into a computation device for executing a relaxation state evaluation method, wherein the relaxation state evaluation method comprises steps:

measuring electrocardiograph (ECG) data of a user;

analyzing the ECG data to generate a first parameter, a second parameter, a third parameter and a fourth parameter, wherein the first parameter is a short-scale entropy slope before a cardiovascular disease treatment (CVDT) of the user; the second parameter is a difference of a post-CVDT mean RR interval and a pre-CVDT mean RR interval; the third parameter is a logarithm of a variance of a pre-CVDT high frequency normal to normal (NN) intervals; the fourth parameter is a logarithm of a ratio of a variance of a pre-CVDT low frequency NN intervals to the variance of the pre-CVDT high frequency NN intervals; the evaluation index is a function of the first parameter, the second parameter, the third parameter and the fourth parameter; the user is determined to in a relaxation state if the evaluation index is over a threshold;

calculating an evaluation index, which is a function of the first parameter, the second parameter, the third parameter and the fourth parameter; and evaluating a relaxation state of the user, wherein the user is determined to be in a relaxation state if the evaluation index is over a threshold.

26. The computer program product according to claim 25, wherein the evaluation index is calculated according to Equation (1):

$$A0+A1{\times}PA1+A2{\times}PA2+A3{\times}PA3+A4{\times}PA4 \quad (1)$$

wherein A0-A4 are coefficients; PA1-PA4 are respectively the first parameter, the second parameter, the third parameter and the fourth parameter.

27. The computer program product according to claim 26, wherein the function for calculating the evaluation index further includes a fifth parameter, which is a pre-CVDT long-scale entropy slope; the evaluation index is calculated according to Equation (2):

$$A0+A1{\times}PA1+A2{\times}PA2+A3{\times}PA3+A4{\times}PA4+A5{\times}PA5 \quad (2)$$

wherein A5 is a coefficient and PA5 is the fifth parameter.

28. The computer program product according to claim 27, wherein the function for calculating the evaluation index further includes a sixth parameter, which is a logarithm of a difference of a post-CVDT NN interval over 20 ms and a pre-CVDT NN interval over 20 ms; the evaluation index is calculated according to Equation (3):

$$A0+A1{\times}PA1+A2{\times}PA2+A3{\times}PA3+A4{\times}PA4+A5{\times}PA5+\\A6{\times}PA \quad (3)$$

wherein A6 is a coefficient and PA6 is the sixth parameter.

29. The computer program product according to claim 28, wherein the function for calculating the evaluation index further includes a seventh parameter, which is a logarithm of a difference of a standard deviation of a post-CVDT normal sinus rhythm (NSR) interval and a standard deviation of a pre-CVDT NSR interval; the evaluation index is calculated according to Equation (4):

$$A0+A1{\times}PA1+A2{\times}PA2+A3{\times}PA3+A4{\times}PA4+Aa{\times}PA5+\\A6{\times}PA6+A7{\times}PA7 \quad (4)$$

wherein A7 is a coefficient and PA7 is the seventh parameter.

30. The computer program product according to claim 29, wherein the function for calculating the evaluation index further includes an eighth parameter, which is a difference of a post-CVDT short-scale entropy slope and a pre-CVDT short-scale entropy slop; the evaluation index is calculated according to Equation (5):

$$A0+A1{\times}PA1+A2{\times}PA2+A3{\times}PA3+A4{\times}PA4+A5{\times}PA5+\\A6{\times}PA6+A7{\times}PA7+A8{\times}PA8 \quad (5)$$

wherein A8 is a coefficient and PA8 is the eighth parameter.

31. The computer program product according to claim 30, wherein the evaluation index is also dependent on user parameters, which represent physiological data of the user.

32. The computer program product according to claim 31, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (6):

$$A0+A1{\times}PA1+A2{\times}PA2+A3{\times}PA3+A4{\times}PA4+A5{\times}PA5+\\A6{\times}PA6+A7{\times}PA7+A8{\times}PA8+Au1{\times}IP1+Au2{\times}\\IP2+Au3{\times}IP3+Au4{\times}IP4 \quad (6)$$

wherein Aua-Au4 are coefficients; IP1-IP4 are respectively the first input parameter, the second input parameter, the third input parameter and the fourth input parameter.

33. The computer program product according to claim 30, wherein the function for calculating the evaluation index further includes a ninth parameter, which is a difference of a post-CVDT long-scale entropy area and a pre-CVDT long-scale entropy area; the evaluation index is calculated according to Equation (7):

$$A0+A1{\times}PA1+A2{\times}PA2+A3{\times}PA3+A4{\times}PA4+A5{\times}PA5+\\A6{\times}PA6+A7{\times}PA7+A8{\times}PA8+A9{\times}PA9 \quad (7)$$

wherein A9 is a coefficient and PA9 is the ninth parameter.

34. The computer program product according to claim 33, wherein the evaluation index is also dependent on user parameters, which represent physiological data of the user.

35. The computer program product according to claim 34, wherein the user parameters includes a first input parameter, a second input parameter, a third input parameter and a fourth input parameter; the first input parameter is a glomerular filtration rate of the user; the second input parameter represents that the user takes a vein dilator; the third input parameter represents that the user does not take anticoagulation medicine; the fourth input parameter represents that the user has hypertension; the evaluation index is calculated according to Equation (8):

$$A0+A1{\times}PA1+A2{\times}PA2+A3{\times}PA3+A4{\times}PA4+A5{\times}PA5+$$
$$A6{\times}PA6+A7{\times}PA7+A8{\times}PA8+A9{\times}PA9+Au1{\times}$$
$$IP1+Au2{\times}IP2+Au3{\times}IP3+Au4{\times}IP4 \qquad (8)$$

wherein Au1-Au4 are coefficients; IP1-IP4 are respectively the first input parameter, the second input parameter, the third input parameter and the fourth input parameter.

36. The computer program product according to claim 35, wherein the user parameters includes a fifth input parameter, a sixth input parameter, a seventh input parameter, an eighth input parameter, a ninth input parameter, a tenth input parameter, a eleventh input parameter, a twelfth input parameter, a thirteenth input parameter and a fourteenth input parameter; the fifth input parameter represents that the user does not take Digitalis Glycoside; the sixth input parameter is age of the user; the seventh input parameter is a pre-CVDT blood pressure of the user; the eighth input parameter represents that the user suffers hyperlipidemia; the ninth input parameter represents that the user does not take a vein dilator; the tenth input parameter represents that the user takes an anticoagulation medicine; the eleventh input parameter represents that the user suffers a peripheral arterial occlusion disease and has accepted balloon dilation; the twelfth input parameter represents that the user suffers a coronary artery disease but has not accepted cardiac catheterization yet; the thirteenth input parameter represents that the user takes an anti-hyperlipidemia medicine; the fourteenth input parameter represents that the user suffers vessel occlusion but has not accepted cardiac catheterization and balloon dilation yet; the evaluation index is calculated according to Equation (9):

$$A0+A1{\times}PA1+A2{\times}PA2+A3{\times}PA3+A4{\times}PA4+A5{\times}PA5+$$
$$A6{\times}PA6+A7{\times}PA7+A8{\times}PA8+A9{\times}PA9+Au1{\times}$$
$$IP1+Au2{\times}IP2+Au3{\times}IP3+Au4{\times}IP4+Au5{\times}IP5+$$
$$Au6{\times}IP6+Au7{\times}IP7+Au8{\times}IP8+Au9{\times}IP9+Au10{\times}$$
$$IP10+Au11{\times}IP11+Au12{\times}IP12+Au13{\times}IP13+$$
$$Au14{\times}IP14 \qquad (9)$$

wherein Au5-Au14 are coefficients; IP5-IP14 are respectively the fifth input parameter, the sixth input parameter, the seventh input parameter, an eighth input parameter, the ninth input parameter, the tenth input parameter, the eleventh input parameter, the twelfth input parameter, the thirteenth input parameter and the fourteenth input parameter.

* * * * *